(12) United States Patent
Ella et al.

(10) Patent No.: US 11,890,291 B2
(45) Date of Patent: Feb. 6, 2024

(54) AQUEOUS COMPOSITION WITH WATER INSOLUBLE VITAMINS

(71) Applicant: Innova Agri Bio Park Private Limited, Malur (IN)

(72) Inventors: Krishna Murthy Ella, Malur (IN); Kankanallu Shankaranarayana Ravi, Malur (IN)

(73) Assignee: INNOVA AGRI BIO PARK PRIVATE LIMITED, Malur (IN)

( * ) Notice: Subject to any disclaimer, the term of this patent is extended or adjusted under 35 U.S.C. 154(b) by 187 days.

(21) Appl. No.: 17/263,706

(22) PCT Filed: Jul. 25, 2019

(86) PCT No.: PCT/IN2019/050548
§ 371 (c)(1),
(2) Date: Jan. 27, 2021

(87) PCT Pub. No.: WO2020/026264
PCT Pub. Date: Feb. 6, 2020

(65) Prior Publication Data
US 2021/0290640 A1    Sep. 23, 2021

(30) Foreign Application Priority Data
Jul. 30, 2018    (IN) .............................. 201841027257

(51) Int. Cl.
*A61K 31/593*    (2006.01)
*A61P 3/02*    (2006.01)
*A61K 9/51*    (2006.01)

(52) U.S. Cl.
CPC .......... *A61K 31/593* (2013.01); *A61K 9/5153* (2013.01); *A61K 9/5161* (2013.01); *A61K 9/5192* (2013.01); *A61P 3/02* (2018.01)

(58) Field of Classification Search
CPC .. A61K 31/593; A61K 9/5161; A61K 9/5153; A61P 3/02
See application file for complete search history.

(56) References Cited

U.S. PATENT DOCUMENTS 8,968,790 B2 * 3/2015 Mousa ....................... A61K 9/14
2010/0203142 A1 * 8/2010 Zhang ........................ A61K 9/14

FOREIGN PATENT DOCUMENTS

RU    2527042 C1 *    8/2014    ............ A23L 33/15
RU    2527042 C1 *    8/2014
WO    2017216667 A1    12/2017

OTHER PUBLICATIONS

Kummara Madhusudana Rao, Anuj Kumar, Sung Soo Han Poly(acrylamidoglycolic acid) nanocomposite hydrogels reinforced with cellulose nanocrystals for pH-sensitive controlled release of diclofenac sodium Polymer Testing 64 (2017) 175-185 (Year: 2017).*
KummaraMadhusudanaRao,AnujKumar,SungSooHan Poly(acrylamidoglycolicacid)nanocompositehydrogelsreinforcedwithcellulosenanocrystalsforpH-sensitivecontrolledreleaseofdiclofenacsodium PolymerTesting64(2017)175-182 (Year: 2017).*
International Search Report dated Nov. 22, 2019 for PCT/IN2019/050548.
Written Opinion dated Nov. 22, 2019 for PCT/IN2019/050548.
Maria Joo Alves Ramalho: PLGA Nanoparticles as a platform for Vitamin D based cancer therapy. Dissertation. Jul. 2014. pp. 14, 17-18.
Teleki et al; 100 Years of Vitamins: The Science of Formulation is the Key to Functionality. KONA Powder and Particle Journal. 2013. vol. 30 pp. 144-163.
V. K. Thakur et al. (eds.), Nanogels of Natural Polymers. Polymer Gels, Gels Horizons: From Science to Smart Materials. 2018. chapter 4. pp. 71-110. https://doi.org/10.1007/978-981-10-6080-9_4.

* cited by examiner

*Primary Examiner* — Robert A Wax
*Assistant Examiner* — Andre Mach
(74) *Attorney, Agent, or Firm* — Schmeiser, Olsen & Watts, LLP

(57) ABSTRACT

Nanogel and nanoparticles comprising vitamin D encapsulated in agar-agar and a polymer selected from poly(acrylamidoglycolic acid) and pectin are provided. Also provided is aqueous nanogel compositions which can be used for prevention or treatment of vitamin D deficiency and methods for encapsulating vitamin D in nanogels and nanoparticles. The nanogel and nanoparticles and compositions thereof are cost-effective, have a considerable shelf life, a faster rate of absorption in the body leading to faster bioavailability. Further, the nanogels and nanoparticles are made with vegetarian sources and causes no changes in the organoleptic properties. The Vitamin D nanogels and nanoparticles developed can be used for fortification of any food, aqueous medium or beverage, including bottled drinking water.

21 Claims, 5 Drawing Sheets

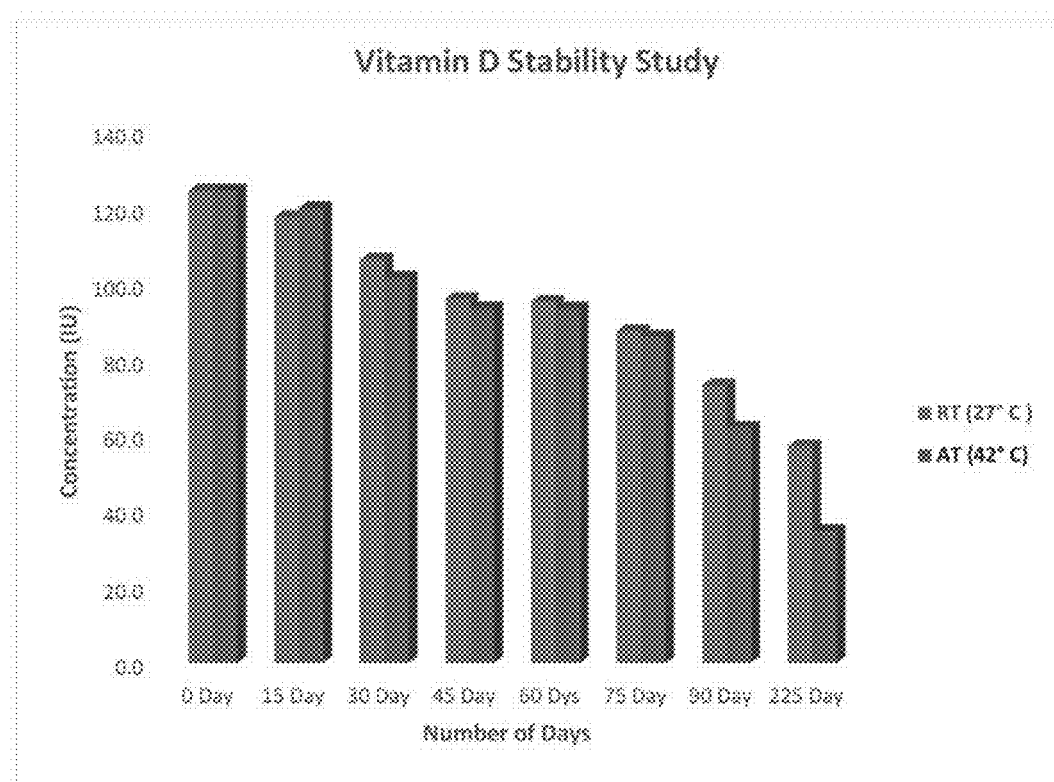
FIGURE 1: Stability studies of formulated Vitamin D aqueous composition

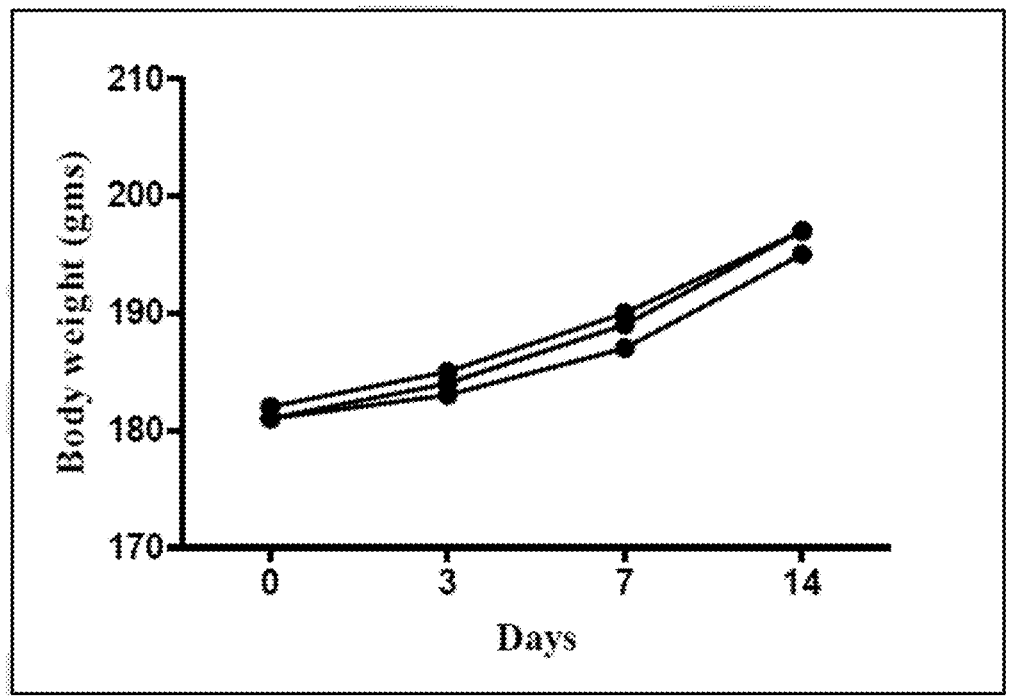
FIGURE 2: Body weight of animals recorded during acute oral toxicity studies

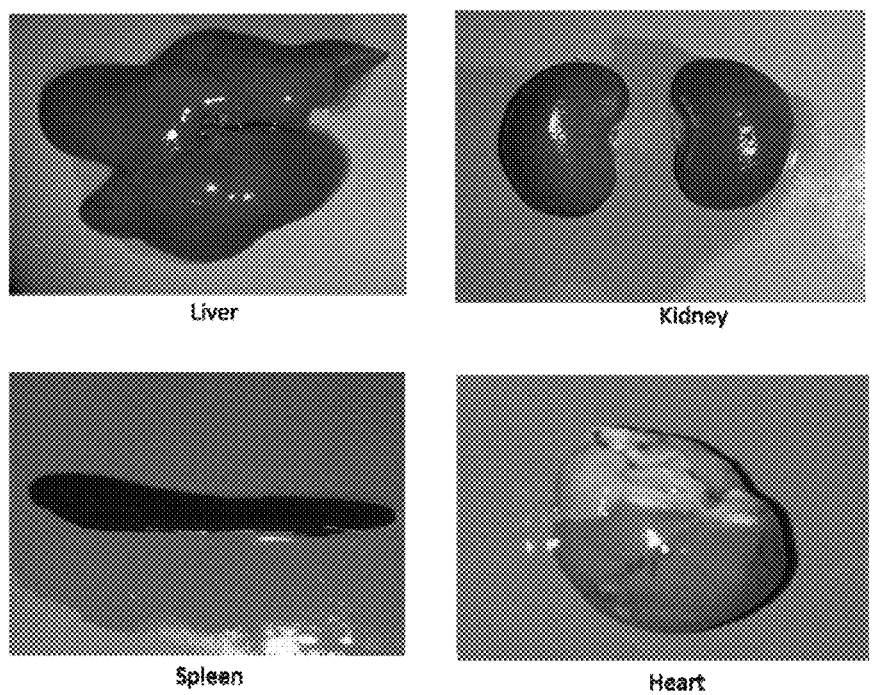
FIGURE 3: Results of gross pathological examinations conducted to check macroscopic alterations in the animal organs.

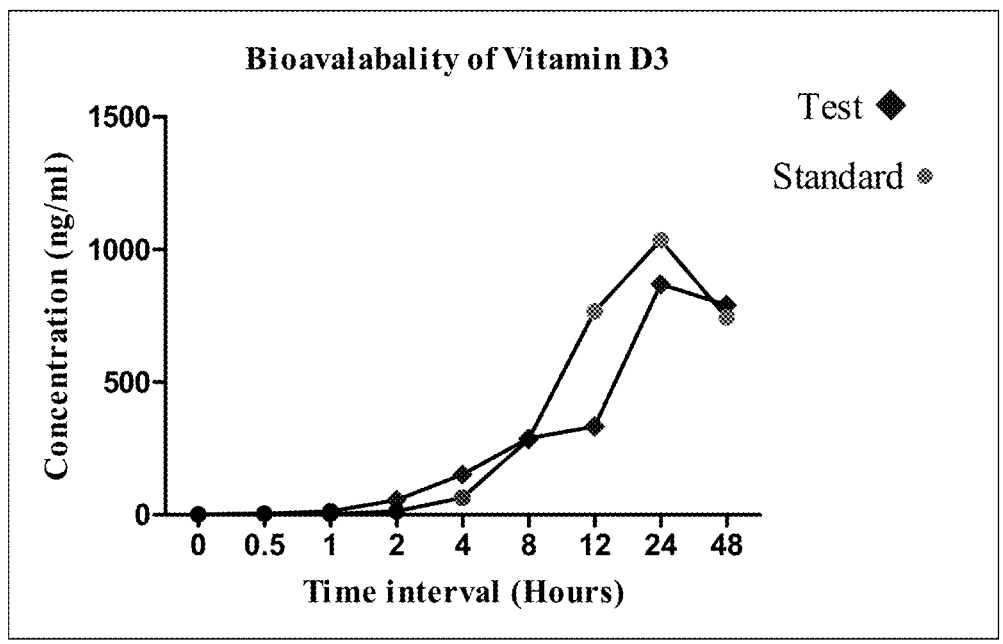
FIGURE 4: Plasma concentration of test substance and the standard drug recorded during pharmacokinetic profiling studies.

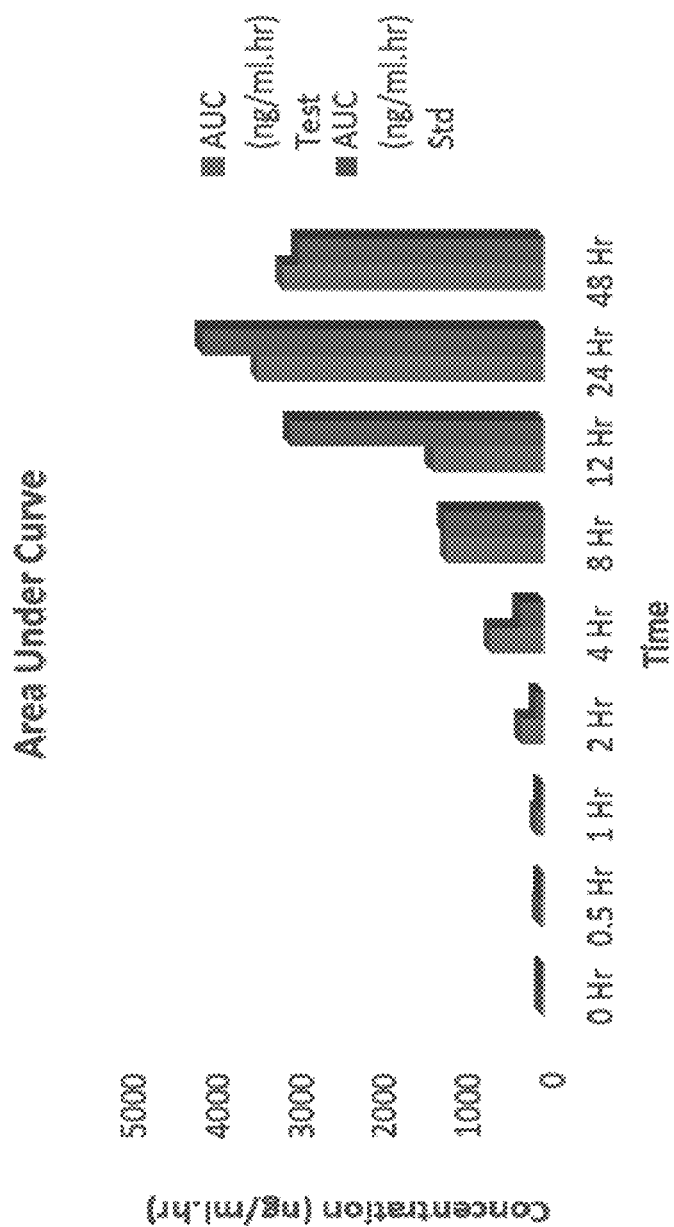
FIGURE 5: Area under the plasma drug concentration-time curve (AUC) calculated for the test substance and the standard drug recorded during pharmacokinetic profiling studies.

AQUEOUS COMPOSITION WITH WATER INSOLUBLE VITAMINS

CROSS-REFERENCE TO RELATED APPLICATIONS

This application claims priority to PCT Application No. PCT/IN2019/050548, having a filing date of Jul. 25, 2019, which is based on IN 201841027257, having a filing date of Jul. 30, 2018, the entire contents both of which are hereby incorporated by reference.

FIELD OF TECHNOLOGY

The following pertains to the field of nanogels/nanoparticles and aqueous compositions thereof. More particularly, the following relates to nanogels and nanoparticles comprising vitamin D and compositions comprising vitamin D nanogels and nanoparticles.

BACKGROUND

Vitamin D deficiency and insufficiency has been a global health issue which is estimated to be affecting more than one billion people across the world. Vitamin D deficiency has been associated with a number of acute and chronic physiological disorders which includes childhood dental caries, periodontitis, autoimmune disorders, infectious diseases, cardiovascular disease, different types of malignancies, type-2 diabetes and neurological disorders.

Vitamin D is produced in the skin on exposure to sunlight. Though, sun exposure alone is ought to be sufficient to attain vitamin D sufficiency in the body, insufficient exposure to sunlight leads to the deficiency. This is coupled by the factor that there are very few dietary sources of Vitamin D, such as flesh of fatty fish, salmon, tuna and mackerel, fish liver oils, beef liver, cheese, egg yolks and mushrooms. Even the limited dietary sources which are available are mostly non-vegetarian sources and is not suited for vegetarian people.

Vitamin D3 (cholecalciferol) or vitamin D2 (ergocalciferol) have been used in the past as supplements or for fortification of widely consumed staple foods to combat Vitamin D deficiency. However, the approaches used for combating vitamin D deficiency till date suffers from one or more of the following drawbacks:

The shelf life of vitamin D fortified foods are very short and vitamin D is not stable for a considerable time period.

The drug compliance/adherence rates are poor, specifically for vitamin D supplements, leading to over dosage or under dosage.

Cholecalciferol (Vitamin D3) is a hydrophobic molecule and cannot be easily fortified in aqueous medium, beverages or food compositions.

The absorption rate and time taken for absorption of Vitamin D3 is low, which leads to low bioavailability for a considerable period after administration.

Commercially available Vitamin D supplements are costly and not easily affordable by people from middle income or low-income economies.

Natural dietary supplements of vitamin D are mostly from non-vegetarian sources.

Though different approaches have been tried as mentioned above, effective delivery of vitamin D has remained a challenge. In view of the same, the inventors have identified that water or aqueous beverages can serve as an important vehicle for delivery of vitamin D. In order to adapt vitamin D for delivery through water or aqueous beverages, the inventors have contemplated an approach for development of vitamin D nanogels and nanoparticles which are hydrophilic in nature and easily disperses in aqueous media.

The nanogels and nanoparticles developed are cost-effective, have a considerable shelf life and a faster rate of absorption in the body which leads to a faster bioavailability. Further, the nanogels and nanoparticles are made with vegetarian and non-vegetarian sources and causes no changes in the organoleptic properties. The Vitamin D nanogels and nanoparticles developed can be used for fortification of any aqueous medium or beverage, including bottled drinking water. Bottled drinking water fortified with vitamin D can work as a replacement for the regular drinking water which can potentially lead to better patient compliance.

SUMMARY

An aspect relates to a nanoparticle encapsulating Vitamin D, wherein the nanoparticle is selected from a group comprising nanogel or PLGA nanoparticle.

Another aspect of embodiments of the invention is to provide a method for the preparation of encapsulated Vitamin D nanogels.

Yet another aspect of embodiments of the invention is to provide a method for the preparation of encapsulated Vitamin D PLGA nanoparticles.

An aspect of embodiments of the invention is to provide a nanoparticle encapsulating Vitamin D, wherein the nanoparticle is selected from a group comprising nanogel or PLGA nanoparticle, and wherein the Vitamin D is present in an amount of 5 to 8 wt % of the nanogel or the Vitamin D is present in an amount of 2 to 4 wt % of the PLGA nanoparticle, dispersed in a medium.

In some embodiments of the invention, there is provided a nanogel comprising Vitamin D and encapsulated in agar-agar and a polymer selected from a group comprising poly(acrylamidoglycolic acid) and pectin. In some embodiments, the agar-agar may be present in an amount of 30 to 35 wt % of the nanogel. In some other embodiment, the polymer is present in an amount of 45 to 50 wt % of the nanogel. In some other embodiment, there is provided a composition comprising nanogels according to embodiments of the invention, wherein the concentration of nanogels dispersed in the medium is in the range from 0.15 mg/L to 0.45 mg/L.

In some other embodiments, the Vitamin D present in the composition is cholecalciferol. In some embodiments, there is provided a composition comprising nanoparticles according to embodiments of the invention, wherein concentration of the PLGA nanoparticles according to embodiments of the invention is 0.35 mg/L to 1 mg/L.

In yet another embodiment, the composition comprises one or more pharmaceutically acceptable excipients or carriers. In some embodiments, the medium of the composition according to embodiments of the invention is an aqueous medium.

In another aspect of embodiments of the invention, there is provided a method for preparation of encapsulated Vitamin D nanogels, comprising:

a. preparing a reaction mixture comprising agar-agar, methylene bisacrylamide, Vitamin D and a monomer or polymer selected from a group comprising poly(acrylamidoglycolic) acid or pectin, wherein the concentration of Vitamin D in reaction mixture is in a range from 5 wt % to 8 wt %;
b. adding potassium per sulphate to the reaction mixture;
c. adding the reaction mixture to a sodium dodecyl sulphate solution;
d. degassing the reaction mixture with nitrogen;
e. adding glutaraldehyde to the reaction mixture; and
f. subjecting the reaction mixture to centrifugation to obtain encapsulated Vitamin D nanogels.

In some embodiments, the vitamin D used in the above-described method for the preparation of encapsulated Vitamin D nanogels is cholecalciferol. In some embodiments, the concentration of agar-agar in reaction mixture of the above-described method for the preparation of encapsulated Vitamin D nanogels is in a range from 9.9 mg/mL to 11.0 mg/mL. In some other embodiments, the concentration of the monomer or polymer in the reaction mixture of the above-described method for the preparation of encapsulated Vitamin D nanogels is in a range from 14 mg/mL to 16 mg/mL. In some embodiments, the step of degassing in the method for the preparation of encapsulated Vitamin D nanogels is done at a temperature in the range from 75° C. to 85° C., for example, at 80° C. and dried at 40° C. In some other embodiments, the centrifugation in the method for the preparation of encapsulated Vitamin D nanogels is performed at a speed in the range from 14500 to 15500 rpm. In some embodiments, the concentration of glutaraldehyde in the method for the preparation of encapsulated Vitamin D nanogels is in the range from 0.5 to 1.5 wt %.

In another aspect of embodiments of the invention, there is provided a method for preparation of encapsulated Vitamin D PLGA nanoparticles, comprising:
a. preparing a reaction mixture of PLGA with Vitamin D dissolved in ethyl acetates solution;
b. dropwise addition of Pluronics to the reaction mixture of step (a) followed by sonication of the emulsion under ice bath;
c. solubilizing the emulsion by magnetic stirring at 1000 rpm for 2.5 hours at 25° C.;
d. filtration of emulsion;
e. cooling of the emulsion at 4° C. during overnight at final concentration of 10 mg/mL; and
f. centrifugation at 15000 rpm for 30 minutes and resuspension in ultrapure water.

In some embodiments, the vitamin D in the method for preparation of encapsulated Vitamin D PLGA nanoparticles is cholecalciferol.

In some embodiments, the nanoparticles are used for the preparation of an aqueous composition.

In some other embodiments, the nanoparticles are used as a fortifying agent in food, beverage and pharmaceutical compositions.

In other embodiments, there is provided a method of treating a subject suffering from vitamin D deficiency by administration of a pharmaceutically effective amount of the composition according to embodiments of the invention.

BRIEF DESCRIPTION

Some of the embodiments will be described in detail, with references to the following Figures, wherein like designations denote like members, wherein:

FIG. 1 depicts stability studies of formulated Vitamin D aqueous composition;

FIG. 2 depicts body weight of animals recorded during acute oral toxicity studies;

FIG. 3 depicts results of gross pathological examinations conducted to check macroscopic alterations in the animal organs;

FIG. 4 depicts plasma concentration of test substance and the standard drug recorded during pharmacokinetic profiling studies; and FIG. 5 depicts area under the plasma drug concentration-time curve (AUC) calculated for the test substance and the standard drug recorded during pharmacokinetic profiling studies.

DETAILED DESCRIPTION

Embodiments described herein can be understood more readily by reference to the following detailed description, examples, and drawings. Elements, apparatus and methods described herein are merely illustrative of the principles of embodiments of the present invention and are not limited to the specific embodiments presented in the detailed description, examples, and drawings. Numerous modifications and adaptations will be readily apparent to those of skill in the art without departing from the spirit and scope of embodiments of the invention.

Unless defined otherwise, all technical and scientific terms used herein have the same meaning as commonly understood by one of ordinary skill in the art to which the methods belong. Although any nanogels, compositions or methods similar or equivalent to those described herein can also be used in the practice or testing of the embodiments of the present invention, representative illustrative methods and compositions are now described.

Where a range of values is provided, it is understood that each intervening value between the upper and lower limit of that range and any other stated or intervening value in that stated range, is encompassed within by the methods and compositions. The upper and lower limits of these smaller ranges may independently be included in the smaller ranges and are also encompassed within by the methods and compositions, subject to any specifically excluded limit in the stated range. Where the stated range includes one or both of the limits, ranges excluding either or both of those included limits are also included in the methods and compositions.

It is appreciated that certain features of the methods, which are, for clarity, described in the context of separate embodiments, may also be provided in combination in a single embodiment. Conversely, various features of the methods and compositions, which are, for brevity, described in the context of a single embodiment, may also be provided separately or in any suitable sub-combination. It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other embodiments without departing from the scope or spirit of the present methods. Any recited method can be carried out in the order of events recited or in any other order that is logically possible.

The term "nanogel" means a particle prepared with one or more polymeric component having any shape with an equivalent diameter of approximately a few to about 100 nm. Nanogels are typically soluble in the solvent in which they are made and nanogels may be further made to be soluble in various liquids as necessary depending on the monomers or polymers used in their manufacture. However, nanogels can also be prepared in the absence of solvent and subsequently dissolved in an appropriate solvent. Nanogels can be used for encapsulating one or more hydrophobic agents. As used herein, the term refers to a hydrophilic polymer particulate encapsulating cholecalciferol. The monomers and polymers used for the purposes of embodiments of the present invention are agar-agar, poly(acrylamidoglycolic) acid and pectin.

The term "nanoparticles" means ultrafine unit with dimensions measured in nanometres (nm; 1 nm=$10^{-9}$ metre). Nanoparticles exist in the natural world and are also created as a result of human activities. Because of their sub microscopic size, they have unique material characteristics, and manufactured nanoparticles may find practical applications in a variety of areas, including medicine, engineering, catalysis, and environmental remediation.

The term "encapsulated" as used herein means that the active agent (vitamin D) is located inside, or in the internal phase or core of the nanogels of embodiments of the present invention and is completely surrounded by one or more polymeric component.

The term "dispersed" as used herein includes the reasonably uniform or homogeneous distribution of the nanogels as described herein in any medium, may be an aqueous medium.

The term "aqueous medium" refers to a medium comprising water wherein water may be the dissolving medium. As used herein, the term includes bottled water, beverages, pharmaceutical compositions, food items having water as a substantial component etc.

The term "degassing" refers to the removal of at least a proportion of the total amount of reactive gas or gases. As used herein, the term means removal of reactive gases by introduction of a non-reactive gas such as nitrogen or argon.

The phrase "pharmaceutically acceptable carrier" or "pharmaceutically acceptable excipient" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose or sucrose; (2) starches, such as corn starch or potato starch; (3) cellulose and its derivatives, such as sodium carboxymethyl cellulose, ethyl cellulose or cellulose acetate; (4) powdered tragacanth; (5) malt; (6) gelatin; (7) talc; (8) excipients, such as cocoa butter or suppository waxes; (9) oils, such as peanut oil, cottonseed oil, safflower oil, sesame oil, olive oil, corn oil or soybean oil; (10) glycols, such as propylene glycol; (11) polyols, such as glycerin, sorbitol, mannitol or polyethylene glycol; (12) esters, such as ethyl oleate or ethyl laurate; (13) agar; (14) buffering agents, such as magnesium hydroxide or aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "fortifying" as used herein refers to the process of either increasing the level of vitamin D that is normally found in a food, beverage or pharmaceutical composition to levels above the natural levels of that food, beverage or pharmaceutical composition, or of introducing vitamin D not normally found in the food, beverage or pharmaceutical composition.

The term "pharmaceutically effective amount" or "effective amount" as used herein refers to an amount, which has a therapeutic effect or is the amount required to produce a therapeutic effect in a subject.

The term "Pluronics" also known as poloxamers, as used herein are a class of synthetic block copolymers which consist of hydrophilic poly(ethylene oxide) (PEO) and hydrophobic poly(propylene oxide) (PPO), arranged in an A-B-A triblock structure, thus giving PEO-PPO-PEO.

As used herein, the term "subject" refers to an animal, for example a mammal, including a human or non-human suffering from vitamin D deficiency.

Embodiments of the invention disclose nanogels, nanoparticles, nanogel compositions, nanoparticles compositions and methods for effective preparations thereof. In particular, embodiments of the invention disclose nanogels and aqueous nanogel compositions prepared using agar-agar and poly(acrylamidoglycolic) acid for effective encapsulation and delivery of vitamin D.

Embodiments of the invention contemplate a multidimensional approach in development of highly efficacious and cost-effective nanogels encapsulating vitamin D. The nanogels of embodiments of the present invention overcomes the problems of the conventional art and can be used for fortifying aqueous compositions, food and beverage compositions as well as pharmaceutical compositions.

The nanogels of embodiments of the present invention are characterized by the following advantages:
1. Miscibility in aqueous medium: The nanogels and nanoparticles of embodiments of the present invention are highly miscible in water and can be used for effective delivery of vitamin D (cholecalciferol in particular) as fortifying agents in edible items such as food, beverages, bottled water as well as pharmaceutical compositions. The disadvantages presented by vitamin D, a hydrophobic component immiscible in aqueous medium, are overcome.
2. High stability and shelf life: The nanogels and nanoparticles of embodiments of the present invention have high stability and shelf life as exhibited from the stability studies conducted. Aqueous compositions fortified with vitamin D nanogels and nanoparticles are stable up to 225 days at room temperature (as shown in Example 4). Consequently, bottled distilled water fortified with vitamin D nanogels and nanoparticles would have a high shelf life. The high stability of the nanogels and nanoparticles makes it a potential fortifying agent for food and beverage products.
3. Potential to improve drug compliance: A major issue with the administration of supplements is the poor drug compliance/adherence rates, which leads to underdosage. Water being the most essential need for every human being can be used as a delivery vehicle for vitamin D, which would lead to high compliance/adherence rates.
4. High absorption and faster release: The nanogels and nanoparticles of embodiments of the present invention are able to release entrapped vitamin D faster resulting in an enhanced absorption rate leading to higher bioavailability up to 8 hours from intake as exhibited in the in vivo bioavailability and kinetic profiling studies conducted (as shown in Example 7).
5. No visible side effects: The nanogels and nanoparticles of embodiments of the present invention have high safety profile as seen from the in vivo acute oral toxicity studies conducted (Example 6).
6. Cost-effective: The nanogels and nanoparticles of embodiments of the present invention are highly cost effective as compared to commercially available vitamin D supplements. Further, water is the cheapest vehicle which can be used for drug delivery. Water fortified with vitamin D can be made available to people from a wide range of socio-economic background across developed as well developing countries.
7. Vegetarian source and no change in organoleptic properties of water: The nanogels and nanoparticles of embodiments of the present invention can be prepared from either vegetarian or non-vegetarian sources. Further, the nanogels and nanoparticles are tasteless and does not cause any change in the organoleptic properties of the fortified drinking water, beverages or food.

Before the nanogels and nanoparticles, compositions and methods of the present disclosure are described in greater detail, it is to be understood that embodiments of the invention are not limited to particular embodiments and may vary. It is also to be understood that the terminology used herein is for the purpose of describing particular embodiments only and is not intended to be limiting.

Vitamin D of embodiments of the present invention also includes within its scope all types of vitamin D such as Vitamin D2 (ergocalciferol), Vitamin D3 (cholecalciferol) or its various analogues, i.e., vitamers (natural analogues) and synthetic analogues. Vitamin D1, a molecular compound of ergocalciferol (D2) with lumisterol in a 1:1 ratio is also used. Vitamin D2 (ergocalciferol) is produced by invertebrates, some plants, and fungi. Biological production of D2 is stimulated by ultraviolet light. Vitamin D3 (cholecalciferol) is synthesized in the skin by the reaction of 7-dehydrocholesterol with UVB radiation, present in sunlight with an UV index of three or more. Vitamin D4 is an analogue scientifically known as 22-dihydroergocalciferol. Vitamin D5 (sitocalciferol) is an analogue created from 7-dehydrositosterol.

In one embodiment, the invention provides a nanogel and nanoparticles comprising vitamin D. In some other embodiments, the Vitamin D present in the compositions according to embodiments of the invention is cholecalciferol.

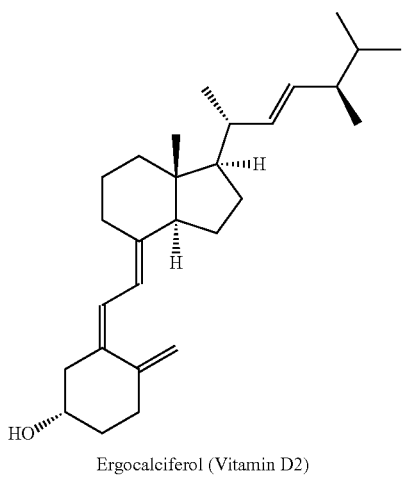

Ergocalciferol (Vitamin D2)

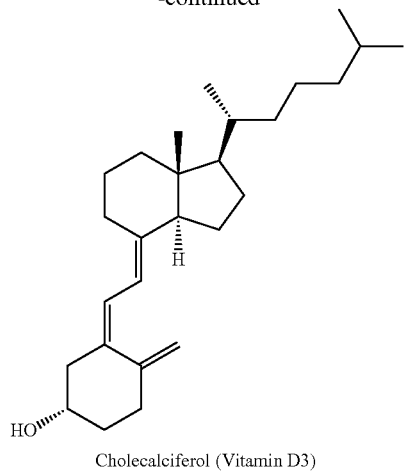

Cholecalciferol (Vitamin D3)

An aspect of embodiments of the invention is to provide a nanoparticle encapsulating Vitamin D, wherein the nanoparticle is selected from a group comprising nanogel or PLGA nanoparticle, and wherein the Vitamin D is present in an amount of 5 to 8 wt % of the nanogel or the Vitamin D is present in an amount of 2 to 4 wt % of the PLGA nanoparticle, dispersed in a medium.

In one embodiment, the invention provides for a nanogel and nanoparticles comprising vitamin D crosslinked with one or more monomers or polymers.

In another embodiment, the invention provides for a nanogel and nanoparticles comprising vitamin D crosslinked with agar-agar and another suitable monomer or polymer.

In a further embodiment, the nanogel and nanoparticles comprising vitamin D is encapsulated in agar-agar and a second monomer or polymer selected from poly(acrylamidoglycolic) acid, pectin and the like.

In some embodiments, the concentration of the PLGA nanoparticles is 0.35 mg/L to 1 mg/L.

In certain embodiments, the nanogels and nanoparticles comprising vitamin D and encapsulated in agar-agar and a second monomer or polymer selected from poly(acrylamidoglycolic) acid or pectin are cross-linked using one or more suitable cross-linkers.

In certain embodiments, the cross-linkers used are selected from a group comprising methylene bisacrylamide and glutaraldehyde.

In certain embodiments, the weight percentage of vitamin D in the nanogel is about 5% to 5.5%, about 5.5% to about 6%, about 6% to 6.5%, about 6.5% to about 7%, about 7% to 7.5%, about 7.5% to about 8%.

In some embodiments, the agar-agar in the nanogel is present in an amount of 30 to 35 wt % of the nanogel. In certain embodiments, the weight percentage of agar-agar in the nanogel is about 30% to 31%, about 31% to 32%, about 32% to 33%, about 33% to 34%, about 34% to 35%.

In some other embodiments, the polymer in the nanogel is present in an amount of 45 to 50 wt % of the nanogel. In certain embodiment, the weight percentage of poly(acrylamidoglycolic) acid or pectin in the nanogel is about 45% to 46%, about 46% to 47%, about 47% to 48%, about 48% to 49%, about 49% to 50%.

In certain embodiments, the concentration of vitamin D in the nanoparticles is about 1 to 1.5% about 1.5 to 2.0%2.0 to 2.5% about 2.5 to 3.0% about 3.0 to 3.5% about 3.5 to 4%.

In another embodiment, the invention provides for the preparation of a composition of nanogels comprising vitamin D crosslinked with one or more monomers or polymers.

The Recommended Dietary Allowances of vitamin D intake ranges from 400-800 IU or 10 to 20 µg. Studies have indicated that a daily vitamin D intake of 1000-4000 IU or 25-100 µg is recommended. 4000 IU is the safe upper limit according to the Institute of Medicine (TOM). For the purposes of embodiments of the invention, a concentration of nanogel in the aqueous composition ranges between 10 µg/L to 30 µg/L which corresponds to 400-1200 IU/L of vitamin D.

In certain embodiments, the concentration of Vitamin D in the composition ranges from about 10 µg/L to 12 µg/L, about 12 µg/L to 14 µg/L, about 14 µg/L to 16 µg/L, about 16 µg/L to 18 µg/L, about 18 µg/L to 20 µg/L, about 20 µg/L to 22 µg/L, about 22 µg/L to 24 µg/L, about 24 µg/L to 26 µg/L, about 26 µg/L to 28 µg/L, about 28 µg/L to 30 µg/L.

In some embodiments, there is provided a composition comprising nanogel, wherein the concentration of nanogels dispersed in the medium is in the range from 0.15 mg/L to 0.45 mg/L.

In some other embodiments, there is provided a composition comprising nanoparticles according to embodiments of the invention, wherein the concentration of the PLGA nanoparticle is 0.35 mg/L to 1 mg/L.

In certain embodiments, the concentration of nanogels in the composition ranges from about 0.15 mg/L to 0.45 mg/L and the concentration of PLGA nanoparticle in the composition ranges from about 0.35 mg/L to 1.0 mg/L.

The composition comprising nanogel and PLGA nanoparticles of embodiments of the present invention may further comprise one or more pharmaceutically acceptable carrier or excipient. The carriers include, but are not limited to sterile aqueous media, solid diluents or fillers, excipients, and various non-toxic organic solvents. In some embodiments, the medium of the composition according to embodiments of the invention is an aqueous medium.

The nanogel and PLGA nanoparticles compositions as disclosed herein can be used as a medicament or as a component in a pharmaceutical composition. Pharmaceutical compositions include tablets, capsules, pills, powders, granules, aqueous and non-aqueous oral solutions and suspensions, hard candies, lozenges, troches, sprays, salves, suppositories, gels, pastes, ointments, jellies, lotions, injectable solutions, elixirs, syrups, and parenteral solutions packaged in containers adapted for subdivision into individual doses.

Parenteral formulations include pharmaceutically acceptable aqueous or non-aqueous solutions, dispersion, emulsions, suspensions, and sterile powders for the preparation thereof. Non-limiting examples of carriers include water, ethanol, polyols (such as propylene glycol, polyethylene glycol), vegetable oils, and injectable organic esters such as ethyl oleate. Fluidity can be maintained by the use of a coating such as lecithin, a surfactant, or maintaining appropriate particle size. Exemplary parenteral administration forms include solutions or suspensions of the compounds of embodiments of the invention in sterile aqueous solutions, for example, aqueous propylene glycol or dextrose solutions. Such dosage forms can be suitably buffered, if desired.

Additionally, lubricating agents such as magnesium stearate, sodium lauryl sulphate and talc may be used if the dried nanogels are used for tableting purposes. Solid compositions of a similar type may also be employed in soft and hard filled capsules. When aqueous suspensions or elixirs are desired for oral administration the nanogels and nanoparticles therein may be combined with various sweetening or flavoring agents, coloring matters or dyes and, if desired, emulsifying agents or suspending agents, together with diluents such as water, ethanol, glycerin, propylene glycol or combinations thereof.

In another embodiment, the nanogels and nanoparticles of embodiments of the present invention are used for fortifying drinking water or any beverage or food. The fortified water or beverage compositions of embodiments of the present invention do not result in development of undesirable colour, solubility or flavor. The nanogels are completely dispersed in water and does not result in an any changes of organoleptic properties. The nanogels and nanoparticles of embodiments of the present invention can be used with solid and semi-solid food as food supplements.

The fortified drinking water compositions of embodiments of the present invention can be prepared from a variety of water sources. Most preferred sources are deionized water, softened water, water treated by commercially available reverse osmosis processes or distilled water.

In one embodiment, small amounts of coloring agents can be optionally used in the fortified water or beverage. Such coloring agents are added to the water for aesthetic reasons only. The exact amount of coloring agent used will vary, depending on the agents used and the intensity desired in the finished product. The amount can be readily determined by one skilled in the art.

In another embodiment, the fortified water or beverage can optionally comprise a flavoring agent or sweetener consisting of any natural or synthetically prepared fruit or botanical flavors or with mixtures of botanical flavors and fruit juice blends. Such flavoring agents or sweeteners are added to the water for aesthetic reasons only. The amount can be readily determined by one skilled in the art.

In another embodiment, the fortified water or beverage can optionally comprise a food grade antioxidant in an amount sufficient to inhibit oxidation of added excipients. Known or conventional food or beverage grade antioxidants can be used.

In another aspect of embodiments of the invention, there is provided a method for preparation of encapsulated vitamin D nanogels, comprising the following steps:
  a. preparing a reaction mixture comprising agar-agar, methylene bisacrylamide, cholecalciferol and a monomer or a polymer selected from a group comprising acrylamidoglycolic acid or pectin, wherein the concentration of Vitamin D in reaction mixture is in a range from 5 wt % to 8 wt %;
  b. adding potassium per sulphate to the reaction mixture;
  c. adding the reaction mixture to a sodium dodecyl sulphate solution;
  d. degassing the reaction mixture with nitrogen;
  e. adding glutaraldehyde to the reaction mixture; and
  f. subjecting the reaction mixture to centrifugation to obtain encapsulated vitamin D nanogels.

In some embodiments, the vitamin D used in the above-described method for the preparation of encapsulated Vitamin D nanogels is cholecalciferol.

In one embodiment, for preparation of vitamin D nanogels reaction mixture comprises agar-agar, poly(acrylamidoglycolic) acid, methylene bisacrylamide and vitamin D.

In one embodiment, agar-agar is dissolved in water by heating to obtain a homogenous mixture.

In some embodiments, the concentration of agar-agar in reaction mixture of the above-described method for the preparation of encapsulated Vitamin D nanogels is in a range from 9.9 mg/mL to 11.0 mg/mL. In one embodiment, the concentration of agar-agar in the reaction mixture ranges from about 9.9 mg/mL to 9.95 mg/mL, from about 9.95 mg/mL to 10.0 mg/mL, from about 10.0 mg/mL to 10.05 mg/mL, from about 10.05 mg/mL to 11.0 mg/mL.

In another embodiment, a monomer or polymer selected from poly(acrylamidoglycolic) acid or pectin is added to the reaction mixture.

In some other embodiments, the concentration of the monomer or polymer in the reaction mixture of the above-described method for the preparation of encapsulated Vitamin D nanogels is in a range from 14 mg/mL to 16 mg/mL. In one embodiment, the concentration of poly(acrylamidoglycolic) acid or pectin in the reaction mixture ranges from about 14 mg/mL to 14.5 mg/mL, from about 14.5 mg/mL to 15 mg/mL, from about 15 mg/mL to 15.5 mg/mL, from about 15.5 mg/mL to 16 mg/mL.

In another embodiment, methylene bisacrylamide is used as a first cross-linker for polymerization of agar-agar to poly(acrylamidoglycolic) acid or pectin.

In one embodiment, the concentration of methylene bisacrylamide in the reaction mixture ranges from about 1.9 mg/mL to 1.95 mg/mL, about 1.95 mg/mL to 2.0 mg/mL, about 2.0 mg/mL to 2.05 mg/mL, about 2.05 mg/mL to 2.1 mg/mL.

In another embodiment, cholecalciferol (vitamin D3) dissolved in acetone-water mixture at a ratio 80:20 was added.

In one embodiment, the concentration of cholecalciferol in the reaction mixture ranges from about 1.9 mg/mL to 1.95 mg/mL, about 1.95 mg/mL to 2.0 mg/mL, about 2.0 mg/mL to 2.05 mg/mL, about 2.05 mg/mL to 2.1 mg/mL.

In yet another embodiment, potassium persulphate or ammonium persulfate is used as an initiator for the polymerization reaction.

In one embodiment, the concentration of potassium persulphate or ammonium persulfate in the reaction mixture ranges from about 0.19 mg/mL to 0.195 mg/mL, about 0.195 mg/mL to 0.2 mg/mL, about 0.2 mg/mL to 0.205 mg/mL, about 0.205 mg/mL to 0.21 mg/mL.

In another embodiment, the reaction mixture is subjected to sodium dodecyl sulfate (SDS) solution.

In another embodiment, the weight percentage of sodium dodecyl sulfate in the nanogel ranges from about 0.4% to 0.45%, about 0.45% to 0.5%, about 0.5% to 0.55%, about 0.5% to 0.6%.

In some embodiments, the step of degassing in the method for the preparation of encapsulated Vitamin D nanogels is done at a temperature in the range from 75° C. to 85° C., for example, at 80° C. and dried at 40° C. In some embodiments, the reaction mixture is subjected to nitrogen gas for a time period in the range from 25 to 35 minutes at a temperature in the range from 75° C. to 85° C.

In another embodiment, the reaction mixture is stirred well at a rotation speed at a range from 900 to 1100 rpm for a time period in the range from 4 hrs to 6 hrs.

In another embodiment, methylene bisacrylamide is added as a second cross-linker to the reaction mixture and the reaction mixture is stirred for a period in the range from 3.5 to 4.5 hrs.

In some embodiments, the concentration of glutaraldehyde in the method for the preparation of encapsulated Vitamin D nanogels is in the range from 0.5 to 1.5 wt %. In one embodiment, the weight percentage of glutaraldehyde in the reaction mixture ranges from about 0.5% to 0.6%, about 0.6% to 0.7%, about 0.7% to 0.8%, about 0.8% to 0.9%, about 0.9% to 1.0%, about 1.0% to 1.1%, about 1.1% to 1.2%, about 1.2% to 1.3%, about 1.3% to 1.4%, about 1.4% to 1.5%.

In some other embodiments, the centrifugation in the method for the preparation of encapsulated Vitamin D nanogels is performed at a speed in the range from 14,500 to 15,500 rpm. In another embodiment, the nanogels are purified by collection through centrifugation at a speed in the range from 14,500 to 15,500 rpm speed for a time period in the range from 8 to 12 min.

In further embodiments, the nanogels are re-dispersed in double distilled water, and the centrifugation cycles are repeated multiple times to remove any unreacted monomers, polymers and cross linkers.

In another aspect of embodiments of the invention, there is provided a method for preparation of encapsulated Vitamin D PLGA nanoparticles, comprising:
  a. preparing a reaction mixture of PLGA with Vitamin D dissolved in ethyl acetates solution;
  b. dropwise addition of Pluronics to the reaction mixture of step (a) followed by sonication of the emulsion under ice bath;
  c. solubilizing the emulsion by magnetic stirring at 1000 rpm for 2.5 hours at 25° C.;
  d. filtration of emulsion;
  e. cooling of the emulsion at 4° C. during overnight at final concentration of 10 mg/mL;
  f. centrifugation at 15000 rpm for 30 minutes and resuspension in ultrapure water.

In some embodiments, the vitamin D in the method for preparation of encapsulated Vitamin D PLGA nanoparticles is cholecalciferol.

In one embodiment, the invention provides for a method of preparing encapsulated vitamin D nanoparticles, comprising the following steps:
  a. The materials of polylactic-ccs-glycolic acid) [(PLGA) (100 mg)] with Vitamin D (10 mg) were dissolved in ethyl acetate solution (1 mL),
  b. An aqueous solution of 1% (w/v) Pluronics (2 mL) was added dropwise to the organic phase. The emulsion was then sonicated under ice bath,
  c. The mixture was placed into 25 mL of 0.1% (w/v) Pluronics,
  d. The next step comprises magnetic stirring at 1000 rpm for 2.5 hours at room temperature to fully solubilize the oil phase with the aqueous phase,
  e. After the evaporation of the organic solvent, the emulsion is filtered (0.2 μm) to exclude aggregates,
  f. The Vitamin D-loaded nanoparticles formed a pellet after the centrifugation (15000 rpm, 30 min) and were resuspended in ultrapure water.

In another embodiment, the purified nanogels are dried at a temperature in the range from 35° C. to 45° C. and stored for further use.

In some embodiments, the nanoparticles are used for the preparation of an aqueous composition.

In some other embodiments, the nanoparticles are used as a fortifying agent in food, beverage and pharmaceutical compositions.

In another embodiment, there is provided a method of treating a subject suffering from vitamin D deficiency by administration of a pharmaceutically effective amount of the composition according to embodiments of the invention.

In another embodiment, the invention provides a method for preventing or treating Vitamin D deficiency by administration of a therapeutically effective amount of vitamin D nanogels and nanoparticles as disclosed herein.

In reference to the treatment or prevention of vitamin D deficiency, an effective amount refers to that amount which has the effect of reducing or inhibiting (that is, slowing to some extent, for example, stopping) one or more signs or symptoms characterizing vitamin D deficiency.

In certain embodiments, nanogel and nanoparticles composition(s) may be administered in one or more dosage forms.

Those skilled in the art will be able to determine, according to known methods, the appropriate amount, dose or dosage of the nanogel and nanoparticles composition for administration to a subject taking into account factors such as age, weight, general health, the compositions administered, the route of administration, the nature and advancement of the vitamin D deficiency requiring treatment, and the presence of other medications.

The nanogel and nanoparticles compositions may be administered together or independently of one another by any route known to a person skilled in the art, such as by oral, intravenous, topical, intraperitoneal or nasal route.

In certain embodiments, the nanogel and nanoparticles compositions are administered at a pre-determined daily dosage. This dosage regimen may be adjusted to provide the optimal therapeutic response. For example, the dose may be proportionally reduced or increased as indicated by the exigencies of the therapeutic situation.

The practice of the method of embodiments of the invention may be accomplished through various administration or dosing regimens. The nanogel and nanoparticles compositions of embodiments of the present invention can be administered intermittently, concurrently or sequentially with other prescribed pharmaceutical compositions.

Repetition of the administration or dosing regimens may be conducted as necessary to achieve the sufficiency of vitamin D levels in the body.

EXAMPLES

Before the nanogels and nanoparticles, compositions and methods of the present disclosure are described in greater detail, it is to be understood that embodiments of the invention are not limited to particular embodiments and may vary. It is also to be understood that the terminology used herein is for the purpose of describing particular embodiments only and is not intended to be limiting.

Example 1: Preparation of Vitamin D Nanogels

For preparation of vitamin D nanogels, a reaction mixture comprising agar-agar, poly(acrylamidoglycolic) acid, methylene bisacrylamide and vitamin D was prepared. For preparing the reaction mixture, 1 g of agar-agar was dissolved in 100 mL water by heating to obtain a homogenous mixture, which was maintained between the concentration range of from 9.9 mg/mL to 11.0 mg/mL, for example, at 10 mg/mL, in the reaction mixture. 1.5 g poly(acrylamidoglycolic) acid was added to the reaction mixture. In another setup, 1.5 g pectin was used instead of poly(acrylamidoglycolic) acid. Thereafter, 200 mg methylene bisacrylamide was added as a cross linker to the reaction mixture. The monomer or polymer was maintained between the concentration range of from 14 mg/mL to 16 mg/mL, for example, at 15 mg/mL, in the reaction mixture 200 mg of vitamin D dissolved in 1 mL acetone-water mixture (80:20) was added. 20 mg potassium persulphate was added as an initiator for the polymerization reaction.

The reaction mixture was transferred to a three necked round bottom flask equipped with a reflux condenser and a nitrogen inlet containing 10 mL sodium dodecyl solution at a concentration of 0.5 wt %. The mixture was bubbled with nitrogen gas for 30 minutes, heated to 80° C., and stirred well at a rotation speed of 1000 rpm for 5 hours. 2 mL glutaraldehyde at a concentration of 1 wt % was added to the reaction mixture as an amine-reactive homobifunctional crosslinker and stirred for a period of 4 hours.

The nanogels were collected by centrifuging the reaction mixture at 15,000 rpm speed for 10 minutes. The nanogels were re-dispersed in double distilled water, and the centrifugation cycles were repeated three times to remove any unreacted monomers, polymers and cross linkers. The purified nanogels were dried at 40° C. and stored in a desiccator for further use.

The prepared nanogels contains agar-agar at 30-35 wt %, poly(acrylamidoglycolic) acid or pectin at 45-50 wt % and cholecalciferol (Vitamin D3) at 5-8 wt % in the dried powder.

The complete preparation and composition of Vitamin D (Cholecalciferol) nanogel is summarized in Table 1.

Example 2: Preparation of Aqueous Composition Comprising Vitamin D Nanogels

For preparing an aqueous composition, the nanogels obtained in Example 1 were dispersed in distilled water. 100 grams of nanogel contains 6.69 g of Vitamin D (Cholecalciferol). The concentration of nanogels in aqueous medium is in the range from 0.15 mg/L to 0.45 mg/L, for example, at 0.22 mg/L.

The fortified water or beverage can optionally comprise a food grade antioxidant in an amount sufficient to inhibit oxidation of added excipients. Known or conventional food or beverage grade antioxidants can be used.

The complete composition of Vitamin D (Cholecalciferol) nanogel in distilled water is depicted in Table 1.

TABLE 1

Preparation and composition of Vitamin D nanogel in water

| Step No. | Activity | Amount of component (mg/mL) | Concentration in process (wt %/vol %/molarity) | % in the final product |
|---|---|---|---|---|
| 1 | Dissolving agar-agar in water | Agar-agar: 1 g Water: 100 mL | Concentration of agar-agar solution: 1 wt %. | 33.44 |
| 2 | Adding Vitamin D (Cholecalciferol) | 200 mg dissolved in 1 mL acetone-water mixture 20% solution | 0.2% | 6.69 |
| 3 | Adding acrylamido glycolic acid | acrylamido-glycolic acid: 1.5 g | 1.50% | 50.17 |
| 4 | Adding methylene bisacrylamide | 200 mg | 0.2% | 6.69 |
| 5 | Adding potassium per sulphate | 20 mg | 0.02% | 0.67 |
| 6 | SDS | 10 ml | 0.5 wt % | 1.67 |
| 7 | Glutaraldehyde | glutaraldehyde: 2 mL | 1 wt % | 0.67 |

Example 3: Preparation of Vitamin D PLGA Nanoparticles

The materials of Poly Lactic-co-Glycolic Acid (PLGA) (100 mg) with vitamin D (10 mg) were dissolved in ethyl acetate solution (1 mL). An aqueous solution of 1% (w/v)

Pluronics (2 mL) was added dropwise to the organic phase. The emulsion was then sonicated under ice bath.

The mixture was placed into 25 mL of 0.1% (w/v) Pluronics. The next step comprises magnetic stirring at 1000 rpm for 2.5 hours at room temperature to fully solubilize the oil phase with the aqueous phase. After the evaporation of the organic solvent, the emulsion is filtered (0.2 µm) to exclude aggregates.

The emulsion is stored at 4° C. during overnight at final concentration of 10 mg/mL, to help in the consolidation of the physical structure of the nanoparticles. The Vitamin D-loaded PLGA nanoparticles formed a pellet after the centrifugation (15,000 rpm, 30 min) and were resuspended in ultrapure water. The same procedure is followed for the unloaded PLGA nanoparticles preparation.

The prepared nanoparticle contains PLGA at 25-35 wt %, cholecalciferol (Vitamin D3) (in 1 ml of Ethylene hydroxide) at 2-4 wt %, Pluronics (2 ml) at 55-65 wt % and Pluronics (25 ml) at 5-10 wt %, in the final preparation/water solution. For preparing an aqueous composition, the PLGA nanoparticles so obtained were dispersed in distilled water. 100 grams of PLGA nanoparticles contains 2.99 g of Vitamin D (Cholecalciferol). The concentration of PLGA nanoparticles in aqueous medium is in the range from 0.35 mg/L to 1 mg/L, for example, at 0.52 mg/L.

The complete preparation and composition of Vitamin D PLGA nanoparticles is summarized in Table 2 below:

TABLE 2

Preparation and composition of Vitamin D nanoparticles in water

| Step No. | Activity | Amount of component (g) | Concentration in process (wt %/vol %/molarity) | % in the final product |
|---|---|---|---|---|
| 1 | PLGA | 0.1 | 10% | 29.85 |
| 2 | vitamin D (1 ml EtOH) | 0.01 | 1% | 2.99 |
| 3 | Pluronics (2 ml) | 0.2 | 1% | 59.70 |
| 4 | Pluronics (25 ml) | 0.025 | 0.1% | 7.46 |

Example 4: Stability Studies of Formulated Vitamin D Aqueous Composition

Stability studies were conducted in order to assess the shelf-life of Vitamin D fortified aqueous composition. The Vitamin D fortified aqueous composition containing 1200 IU/L was evaluated up to 225 days and the concentration of vitamin D in the solution was recorded at room temperature (27±2° C.) and at accelerated temperature (42±2° C.). The results are depicted in Table 3 and FIG. 1.

TABLE 3

Vitamin D stability studies

| Temp | 0 Day | 15 Days | 30 Days | 45 Days | 60 Days | 75 Days | 90 Days | 225 Days |
|---|---|---|---|---|---|---|---|---|
| Room Temperature (27° C.) | 124.5 | 117.6 | 106.4 | 96.0 | 95.3 | 87.5 | 73.3 | 57.2 |
| Accelerated Temperature (42° C.) | 124.5 | 120.0 | 101.6 | 93.7 | 93.6 | 86.2 | 62.1 | 34.8 |

At the end of 225 days, vitamin D concentration was found to be 57.2 IU at room (27° C.) and 34.8 IU accelerated temperature (42° C.). The Vitamin D fortified aqueous composition at 27° C. (Room Temperature) found to stable up to 225 days from the date of preparation in the range (120-55 IU) in 100 ml of bottled water. Thus, the vitamin D fortified aqueous composition has a high shelf life of up to 225 days at room temperature.

Example 5: Microbial Load Determination

A microbial load determination study was conducted after 30 days to check microbial growth in packaged vitamin D fortified aqueous composition. Tests were conducted to check the presence of major pathogenic microorganisms as shown in Table 4.

TABLE 4

Microbial Load Determination
Microbial Study

| Organism | Units |
|---|---|
| Total plate count | <1 cfu/ml |
| Salmonella | Absent/100 ml |
| E. coli | Absent/100 ml |
| S. aureus | Absent/100 ml |
| P. aeruginosa | Absent/50 ml |

No microbial load was observed in the packaged vitamin D fortified aqueous composition indicating that the aqueous composition is safe for intake.

Example 6: Acute Oral Toxicity Studies

Acute oral toxicity studies of vitamin D fortified aqueous composition were conducted as per OECD Guideline for Testing of Chemicals (423). Briefly, a single oral dose of vitamin D fortified aqueous composition at different concentration were administered to two groups of Wister rats as shown in Table 5.

TABLE 5

Toxicity Study

| Groups | Dose | Treatment Description | No. of animals |
|---|---|---|---|
| I | 5 mg/kg | Single dose oral administration 14 Days Observation | 3 |
| II | 50 mg/kg | | 3 |

It was seen that the test substance at 5 mg/kg did not produce any mortality throughout the study period of 14 days but at 50 mg/kg body weight all the three animals showed mortality. Thus, the lethal dose of test substance in female rats after single oral treatment was found to be 50 mg/kg body weight.

The body weight of the live animals was recorded during the period as shown in Table 6 and FIG. 2.

TABLE 6

Body weight of animals at 5 mg/kg dose from Day 0 to Day 14

| Animal ID | Dose | Before Day 0 | After Day 3 | Day 7 | Day 14 |
|---|---|---|---|---|---|
| RA 01 | 5 mg/kg | 181.33 ± 0.33 | 184.00 ± 0.58 | 188.67 ± 0.88 | 196.33 ± 0.67 |
| RA 02 | | | | | |
| RA 03 | | | | | |

It was found that all the surviving animals had gained body weight by 3rd, 7th and 14th day as compared to 0 day which is a normal pattern.

Further, the animals were euthanized at the end of the 14-day period and gross pathological examinations were conducted to check any macroscopic alterations. The results are depicted in Table 7 and FIG. 3.

TABLE 7

Gross pathological examinations

| Animal ID | Dose | Macroscopic lesions |
|---|---|---|
| RA 01 | 5 mg/kg | No macroscopic alteration occurred |
| RA 02 | | No macroscopic alteration occurred |
| RA 03 | | No macroscopic alteration occurred |

No macroscopic alterations were observed for the animals. The study indicates that there were no adverse effects of the vitamin D fortified aqueous composition at an oral dosage of 5 mg/kg body weight.

Example 7: Bioavailability and Pharmacokinetic Profiling of Vitamin D Fortified Water The pharmacokinetic profile and bioavailability of Vitamin D fortified aqueous composition by oral administration in Wistar rats was assessed using LC-MS/MS method.

Test substance (Vitamin D3 fortified aqueous composition) and standard drug cholecalciferol (Vitamin D3) was administered by oral route at the dose of 5 mg/kg body weight to Rats as shown in Table 8.

TABLE 8

Test groups for assessing bioavailability and kinetic profiling

| Groups | Group Description | Treatment Description | Dose Volume (ml/kg) | No. of animals |
|---|---|---|---|---|
| Group 1 | Test (Vitamin D3 fortified Water) | Animals were treated Test substance of Vitamin D3 Water of 5 mg/kg body weight. | 10 | 6 |
| Group 2 | Standard (Cholecalciferol) | Animals were treated Standard of Cholecalciferol of 5 mg/kg body weight. | 10 | 6 |

After oral administration of the test substance and the standard drug, 500 μL of blood sample was collected in EDTA containing tubes at different time intervals of 0, ½, 1, 2, 4, 8, 12, 24 and 48 hours.

The plasma was separated from blood samples for bioanalysis and pharmacokinetic profiling was performed using LC-MS/MS method for the quantification of vitamin D3 in Rat plasma. The plasma concentration of test substance and the standard drug was recorded as shown in Table 9 and FIG. 4.

TABLE 9

Plasma Concentration for Standard vitamin D3 and Test Vitamin D3 Water

| Sl No. | Time (Hr) | Avg concentration of Standard vitamin D3 (ng/ml) | Avg concentration of Test vitamin D3 water (ng/ml) |
|---|---|---|---|
| 1 | 0 | 1.66 ± 1.66 | 2.0 ± 2.0 |
| 2 | 0.5 | 4.16 ± 2.17 | 3.93 ± 2.02 |
| 3 | 1 | 3.70 ± 1.98 | 13.0 ± 4.08 |
| 4 | 2 | 13.40 ± 4.87 | 55.93 ± 8.11 |
| 5 | 4 | 68.83 ± 22.53 | 152.2 ± 16.41 |
| 6 | 8 | 283.9 ± 82.05 | 288.4 ± 63.52 |
| 7 | 12 | 766.7 ± 92.5 | 332.6 ± 106.2 |
| 8 | 24 | 1036 ± 123.1 | 869.6 ± 26.96 |
| 9 | 48 | 744.4 ± 33.61 | 790.1 ± 78.15 |

The results indicate that the test substance (Vitamin D3 fortified Water) exhibits a faster rate of absorption as compared to the standard drug. The bioavailability of vitamin D3 above a threshold of 10 ng/mL in plasma was observed at 1 hour for the test substance, while the same was observed at 2 hours for the standard drug.

The test substance was able to maintain a substantially higher bioavailability for 8 hours after intake as indicated by the data. Further, the bioavailability for both the test substance and the drug were comparable up to 48 hours.

The data indicates that the vitamin D3 provide a faster release resulting in an enhanced absorption rate leading to higher bioavailability at shorter period.

The area under the plasma drug concentration-time curve (AUC) was calculated which reflects the actual body exposure to drug after administration of a dose of the drug. The results are shown in Table 10 and FIG. 5.

TABLE 10

AUC and $AUC_{0-t}$ for Standard Vitamin D3 and Test vitamin D3 water

| Sl No. | Time (Hr) | AUC (ng/ml · hr) Standard vitamin D3 | AUC (ng/ml · hr) Test vitamin D3 water |
|---|---|---|---|
| 1 | 0 | 20 | 21.33 |
| 2 | 0.5 | 43.33 | 50.66 |
| 3 | 1 | 41.66 | 91.33 |
| 4 | 2 | 105.66 | 257.33 |
| 5 | 4 | 288.66 | 631 |
| 6 | 8 | 1180.33 | 1159 |
| 7 | 12 | 3013.66 | 1330.33 |
| 8 | 24 | 4059.33 | 3413 |
| 9 | 48 | 2914.66 | 3104 |
| — | — | $AUC_{0-t}$ = 11667.29 ng/ml · hr | $AUC_{0-t}$ = 10057.98 ng/ml · hr |

The result showed that test substance (vitamin D3 nanogels or nanoparticles) had an oral exposure of area under curve concentration of 10057.98 ng/ml·hr, while the standard drug had an exposure area of 11667.29 ng/ml·hr. The AUC values were clinically comparable and indicated that Vitamin D3 nanogels/nanoparticles were able to maintain the total exposure as compared to a standard drug.

Example 8: Volume of Distribution Test

The volume of distribution ($V_d$) test was done to check the ability of Vitamin D3 nanogels/nanoparticles to distribute through different body fluid compartments. Apparent volume of distribution ($V_d$) was calculated by dividing the amount of the nanogel/nanoparticles and the standard drug administered on the plasma concentration as shown in Table 11.

TABLE 11

Volume of distribution of test substance and standard drug

| Sl No. | Time (Hr) | Test Substance (L/kg) | Standard Drug (L/kg) |
|---|---|---|---|
| 1 | 0 | 277.8 ± 277.8 | 333.3 ± 333.3 |
| 2 | 0.5 | 575.6 ± 295.6 | 548.8 ± 285.8 |
| 3 | 1 | 520.8 ± 221.4 | 632.7 ± 339.6 |
| 4 | 2 | 93.89 ± 15.55 | 465.9 ± 129.3 |
| 5 | 4 | 33.7 ± 3.97 | 96.22 ± 25.47 |
| 6 | 8 | 19.45 ± 4.89 | 20.25 ± 4.58 |
| 7 | 12 | 17.9 ± 4.56 | 6.73 ± 0.89 |
| 8 | 24 | 5.76 ± 0.17 | 4.98 ± 0.67 |
| 9 | 48 | 6.46 ± 0.67 | 6.74 ± 0.31 |

The results showed that the Volume of distribution for vitamin D nanogels/nanoparticles were comparable to standard drug, which indicated that the nanogels/nanoparticles were able to freely distribute through different body fluid compartments.

Although the invention has been illustrated and described in greater detail with reference to the preferred exemplary embodiments, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

We claim:

1. A hydrophilic nanoparticle encapsulating Vitamin D, wherein the hydrophilic nanoparticle is selected from the group consisting of nanogel or PLGA nanoparticle, and wherein the Vitamin D is present in an amount of 5 to 8 wt % of the nanogel or the Vitamin D is present in an amount of 2 to 4 wt % of the PLGA nanoparticle, dispersed in a medium.

2. The hydrophilic nanoparticle encapsulating Vitamin D as claimed in claim 1, wherein the Vitamin D is encapsulated in agar-agar and a polymer selected from the group consisting of poly(acrylamidoglycolic acid) and pectin.

3. The hydrophilic nanoparticle encapsulating Vitamin D as claimed in 2, wherein agar-agar is present in an amount of 30 to 35 wt % of the nanogel.

4. The hydrophilic nanoparticle encapsulating Vitamin D as claimed 2, wherein the polymer is present in an amount of 45 to 50 wt % of the nanogel.

5. The hydrophilic nanoparticle encapsulating Vitamin D as claimed 1, wherein the concentration of nanogels dispersed in the medium is in the range from 0.15 mg/L to 0.45 mg/L.

6. The hydrophilic nanoparticle encapsulating Vitamin D as 1, wherein Vitamin D is cholecalciferol.

7. The hydrophilic nanoparticle encapsulating Vitamin D as claimed 1, wherein the concentration of the PLGA nanoparticle is 0.35 mg/L to 1 mg/L.

8. The hydrophilic nanoparticle encapsulating Vitamin D as claimed in claim 1, forming a composition in combination with one or more pharmaceutically acceptable excipients or carriers.

9. The hydrophilic nanoparticle encapsulating Vitamin D as claimed in claim 1, wherein the medium is an aqueous medium.

10. A method for preparation of encapsulated Vitamin D nanogels, comprising:
   a. preparing a reaction mixture comprising agar-agar, methylene bisacrylamide, Vitamin D and a monomer or polymer selected from a group comprising poly(acrylamidoglycolic) acid or pectin, wherein the concentration of Vitamin D in the reaction mixture is in a range from 5 wt % to 8 wt %;
   b. adding potassium per sulphate to the reaction mixture;
   c. adding the reaction mixture to a sodium dodecyl sulphate solution; d. degassing the reaction mixture with nitrogen;
   e. adding glutaraldehyde to the reaction mixture; and
   f. subjecting the reaction mixture to centrifugation to obtain encapsulated Vitamin D nanogels.

11. The method as claimed in claim 10, wherein Vitamin D is cholecalciferol.

12. The method as claimed in claim 10, wherein the concentration of agar-agar in the reaction mixture is in a range from 9.9 mg/mL to 11.0 mg/mL.

13. The method as claimed in claim 10, wherein the concentration of the monomer or polymer in the reaction mixture is in a range from 14 mg/mL to 16 mg/mL.

14. The method as claimed in claim 10, wherein the step of degassing is done at a temperature in the range from 75° C. to 85° C. and dried at 40° C.

15. The method as claimed in claim 10, wherein centrifugation is performed at a speed in the range from 14500 to 15500 rpm.

16. The method as claimed in claim 10, wherein the concentration of glutaraldehyde is in the range from 0.5 to 1.5 wt %.

17. A method for preparation of encapsulated Vitamin D PLGA nanoparticles, comprising:
   a. preparing a reaction mixture of PLGA with Vitamin D dissolved in ethyl acetates solution;
   b. dropwise addition of Pluronics to the reaction mixture of step (a) followed by sonication of the emulsion under ice bath;
   c. solubilizing the emulsion by magnetic stirring at 1000 rpm for 2.5 hours at 25° C.;
   d. filtration of emulsion;
   e. cooling of the emulsion at 4° C. during overnight at final concentration of 10 mg/mL;
   f. centrifugation at 15000 rpm for 30 minutes and resuspension in ultrapure water.

18. The method as claimed in claim 17, wherein Vitamin D is cholecalciferol.

19. The hydrophilic nanoparticle encapsulating Vitamin D as claimed in claim 1, wherein the nanoparticle is used in an aqueous composition.

20. The hydrophilic nanoparticle encapsulating Vitamin D as claimed in claim 1, wherein the hydrophilic nanoparticle is used as a fortifying agent in at least one of food, beverage and pharmaceutical compositions.

21. A method of treating a subject suffering from vitamin D deficiency by administration of a pharmaceutically effective amount of the hydrophilic nanoparticle encapsulating Vitamin D as claimed in claim 1.

* * * * *